United States Patent [19]

Chorvat et al.

[11] 4,012,391

[45] Mar. 15, 1977

[54] 11β-ALKYL-2-AZAESTRATRIENES AND INTERMEDIATES

[75] Inventors: Robert J. Chorvat, Arlington Heights; Raphael Pappo, Skokie, both of Ill.

[73] Assignee: G. D. Searle & Co., Chicago, Ill.

[22] Filed: Jan. 22, 1975

[21] Appl. No.: 543,027

Related U.S. Application Data

[63] Continuation-in-part of Ser. No. 467,217, May 6, 1974.

[52] U.S. Cl. .................. 260/289 AZ; 260/283 SC; 260/287 AZ; 424/258
[51] Int. Cl.² ....................................... C07D 221/16
[58] Field of Search ... 260/289 AZ, 284 R, 287 AZ

[56] References Cited

UNITED STATES PATENTS 3,887,567  6/1975  Chorvat et al. ............. 260/289 AZ

OTHER PUBLICATIONS

Pappo et al. "Chem. Abstracts", vol. 77, Abstract No. 114648n (1972).
Burger "Medicinal Chemistry" 3rd Ed. part 1, p. 662 Wiley–Interscience (1970).

*Primary Examiner*—Donald G. Daus
*Assistant Examiner*—David B. Springer
*Attorney, Agent, or Firm*—John J. McDonnell

[57] ABSTRACT

11β-Alkyl-2-azaestratrienes, displaying valuable pharmacological properties, e.g. anti-viral and hypolipemic, are manufactured by a total synthesis originating with dihydroresorcinol.

14 Claims, No Drawings

11β-ALKYL-2-AZAESTRATRIENES AND INTERMEDIATES

This application is a continuation-in-part of our copending application Ser. No. 467,217, filed May 6, 1974.

The present invention is concerned with a novel process and novel intermediates useful in the production of 2-azasteroids, which display valuable pharmacological properties, e.g. antiviral and hypolipemic.

The preferred group of compounds is represented by the tetracyclic compounds of the following structural formula

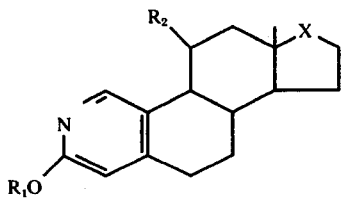

wherein $R_1$ is a lower alkyl or tri(lower alkyl)silyl group having 1 to 7 carbon atoms inclusive or a cycloalkyl group having 4-8 carbon atoms inclusive, $R_2$ is a lower alkyl group having 1 to 4 carbon atoms inclusive, and X is a carbonyl group or a group of the formula

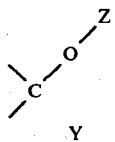

wherein Y is hydrogen, a lower alkyl group having 1 to 7 carbon atoms inclusive, a lower 1-alkynyl group having 2 to 7 carbon atoms inclusive or a propadienyl group and Z is hydrogen or a lower alkanoyl group having 1 to 7 carbon atoms inclusive.

Those compounds are produced from a novel group of intermediates represented by the following structural formulas

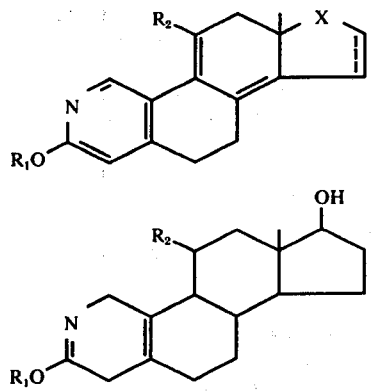

wherein $R_1$ is a lower alkyl group having 1–7 carbon atoms inclusive or a cycloalkyl group having 4–8 carbon atoms inclusive, $R_2$ is a lower alkyl group having 1–4 carbon atoms inclusive, X is a carbonyl or β-hydroxymethylene group, and the dotted line represents an optionally doubly bonded linkage. The lower alkyl groups in the foregoing structural formulas are typified by methyl, ethyl, propyl, butyl, pentyl, hexyl, heptyl and the branched-chain isomers thereof. The cycloalkyl groups represented herein have 4–8 carbon atoms inclusive and are illustrated by cyclobutyl, cyclopentyl, cyclohexyl, cycloheptyl and cyclooctyl. Examples of the lower alkanoyl groups depicted in the above formula are formyl, acetyl, propionyl, butyryl, valeryl, caproyl, heptanoyl and the branched-chain isomers thereof. The lower 1-alkynyl groups represented by the above formula are ethynyl, propynyl, butynyl, pentynyl, hexynyl, heptynyl and the branched-chain isomers derived therefrom.

For purpose of this invention the terms halo or halide refer to those derivatives of bromine, chlorine, fluorine or iodine.

The novel compounds of the present invention originate from a novel process which utilizes dihydroresorcinol as the starting material. That substance thus is allowed to react with a chlorinating reagent such as phosphorus trichloride to afford 3-chloro-2-cyclohexen-1-one. Reaction with cycnoacetamide and sodium hydride results in α-cyano-3-oxo-1-cyclohexen-1-acetamide, which is contacted with a dialkylformamide acetal, for example dimethylformamide diethyl acetal or dimethylformamide dineopentyl acetal, to produce 2,3,5,6,7,8-hexahydro-3,8-dioxo-4-isoquinolinecarbonitrile. Elimination of the cyano group is effected by heating with hydrobromic acid, thus affording 2,3,5,6,7,8-hexahydro-3,8-isoquinolinedione. Heating with an alkyl or cycloalkyl halide produces the corresponding 6-alkoxy and 6-cycloalkoxy 7-aza-1-tetralones together with the N-alkylated or N-cycloalkylated derivatives. Typically, 2,3,5,6,7,8-hexahydro-3,8-isoquinolinedione is heated in benzene at the reflux temperature with methyl iodide and silver carbonate to yield 7-aza-6-methoxy-1-tetralone together with 2-methyl-2,3,5,6,7,8-hexahydro-3,8-isoquinolinedione.

The reaction of the keto group of the 6-alkoxy, and 6-cycloalkoxy 7-aza-1-tetralones with the lithium salt formed by adding butyl lithium to an appropriate halo substituted dimethylaminoalkene affords the corresponding N,N-dimethyl-N-(2-[5,6,7,8-tetrahydro-8-hydroxy-3-alkoxyisoquinol-8-yl]alk2-en-1-yl)amine, or the appropriate cycloalkyloxy derivative. Typically, 7-aza-6-methoxy-1-tetralone is contacted with a solution containing butyl lithium and 2-bromo-3-dimethylaminopropene to yield N,N-dimethyl-N-(2-[5,6,7,8-tetrahydro-8-hydroxy-3-methoxyisoquinol-8-yl]prop-2-en-1yl)amine. The hydroxyl substituent is removed with a phosphorous oxyhalide, such as phosphorous oxychloride in pyridine or in concentrated sulfuric acid, to yield the N,N-dimethyl-N-(2-[5,6-dihydro-3-substituted-isoquinol-8-yl]alk-2-en-1-yl)amine. For example, N,N-dimethyl-N-(2-[5,6,7,8-tetrahydro-8-hydroxy-3-methoxyisoquinol-8-yl]prop-2-en-1-yl)amine is contacted with phosphorous oxychloride in pyridine to obtain N,N-dimethyl-N-(2-[5,6-dihydro-3-methoxyisoquinol-8-yl-]prop-2-en-1-yl)amine. Quaternarization of the amines with an alkyl halide, e.g. methyl iodide, yields the quaternary salts, which are subsequently reacted with silver oxide and then with 2-(lower alkyl)cyclopentane-1,3-dione to yield the appropriate 5,6-dihydro-3-substituted-8-[3-(2-methyl-1,3-dioxocyclopent-2-yl)alk-1-en-2- yl]isoquinoline. In that manner, the aforementioned N,N-dimethyl-N-(2[5,6-dihydro-3-methoxyisoquinol-8-yl]prop-2-en-1-yl)amine is treated with methyl iodide to afford the corresponding trimethyl ammonium iodide. Subsequent treatment with silver oxide and 2-(lower alkyl)cyclopentane-1,3-dione produces 5,6-dihydro-3-methoxy-8-[3-(2-methyl-1,3-dioxocyclopent-2-yl)prop-1-en-2-yl]isoquinoline. Cyclization of the diketones is effected conveniently with sulfuric acid to afford the corresponding dl-2-aza-3-substituted-11β-methylestra-1,3,5(10),8(14),9(11),15-hexaen-17-ones. Representative thereof is the formation of dl-2-aza-3-methoxy-11β-methylestra-1,3,5(10),8(14),9(11),15-hexaen17one upon contacting the aforementioned isoquinoine derivative with sulfuric acid.

Reduction of the 17-ketone moiety with a metallic hydride reducing agent, as for example, diisobutyl aluminum hydride, affords the 17β-ol. Catalytic hydrogenation, using a palladium-on-calcium carbonate catalyst effects saturation of the 15-double bond. Further catalytic reduction utilizing palladium-on-alumina affords those derivatives having the 1,3,5(10), and 8double bonds. Typically dl-2-aza-3-methoxy-11β-methylestra-1,3,5(10), 8(14),9(11),15-hexaen-17-one is reduced with diisobutylaluminum hydride to the 17β-ol corresponding, and then subsequent hydrogenation as described above yields dl-2-aza-3-methoxy-11β-methylestra-1,3,5(10),8-tetraen-17β-ol. Reduction of the 8-double bond then can be accomplished with sodium metal in liquid ammonia to produce the instant compounds, e.g. dl-2-aza-3-methoxy-11β-methylestra-1,3,5(10)trien-17β-ol. A particularly preferred method of producing the instant compounds is to treat the tetraenes with sodium metal in liquid ammonia to produce the corresponding dl-2-aza-11β-alkyl-3-substituted-estra-2,5(10)dien-17β-ols, which then are rearomatized with dichlorodicyanobenzoquinone to yield the desired dl-2-aza-11β-alkyl-3-substututed-estra-1,3,5(10)-trien-17β-ols. Acylation of the 17β-ol derivatives, e.g. with the appropriate acid anhydride in pyridine, affords the 17βalkanoyl derivatives.

Subsequent oxidation of the 17β-ols with sulfur trioxide in pyridine or with chromic acid yields the 17ketones, e.g. dl-2-aza-3-methoxy-11-methylestra-1,3,5(10)trien-17-one. The instant 17β-alkynyl derivatives can the be produced forthwith by the addition of the appropriate 1-alkyne in an appropriate solution, such as tetrahydrofuran and ethanol, containing powdered potassium hydroxide, at low temperature under a nitrogen atmosphere. When acetylene is used, the resultant product is 2-aza17α-ethynyl-3-methoxy-11β-methylestra-1,3,5(10)-trien17β-ol.

Treatment of the 17-ketone azaestratrienes with an alkyl Grignard or alkyl lithium reagents conveniently yields the 17α-alkyl derivatives. One such example is the reaction of 2-aza-3-methoxy-11β-methylestra-1,3,5(10)trien-17-one with methyl magnesium bromide in tetrahydrofuran, thus affording 2-aza-3-methoxy-11β,17α-dimethylestra1,3,5(10)-trien-17β-ol.

The 17α-propadienyl derivatives of this invention are produced from the corresponding 17-keto compounds by reaction with 3-tetrahydropyran-2'-yloxyprop-1-ynyl magnesium bromide followed by reaction, typically with lithium aluminum hydride, of the resulting propynyl carbinol. Specifically, 2-aza-3-methoxy-11β-methylestra-1,3,5(10)trien-17-one is contacted with 3-tetrahydropyran-2'yloxyprop-1-ynyl magnesium bromide and the resulting propynyl carbinol is allowed to react with lithium aluminum hydride to yield 2-aza-3-methoxy-11β-methyl-17αpropadienylestra-1,3,5(10)-trien-17β-ol.

The instant 3-trialkylsilyl derivatives are prepared conveniently from the dl-2-aza-3-alkoxy-11βalkylestra-1,3,5(10)-trien-17-ones by initial treatment with hydrobromic acid to form the dl-2-aza-11β-alkylestra-1(10),4-diene-3,17-diones. Those intermediates are isolated by filtration and subsequently treated with the appropriate trialkylchlorosilane, thereby forming the instant dl-2-aza-11β-alkyl-3-trialkylsilyloxyestra-1,3,5(10)trien-17-ones.

The instant dl-2-aza-11-alkylestra-1,3,5(10)trienes are valuable pharmacological agents as is evidenced by their anti-viral activity and hypolipemic activity. A suitable assay for detection of the anti-viral activity is described as follows:

Cell cultures of primary Rhesus monkey kidney maintained in 25 cc. plastic flasks and each containing test compound in concentrations of 625, 125, 25, 5, or 1μg./ml. are prepared in pairs. These flasks and an identical pair of flasks containing no test compound are each inoculated with a dose of influenza virus type A (Strain 575) previously shown to produce maximum hemadsorption and minimum cytopathogenic effects after a 24-hour incubation. Where the cultures contain test compound the viruses are added 1 hour after addition of the test compound to the culture. After 24 hour incubation of the cultures the supernatant fluids are removed and 3.0 ml. of a 0.4% suspension of guinea pig erythrocytes is added to each flask. The flasks are then incubated at 4° C. in a horizontal position for 30 minutes. The flasks are rocked every 10 minutes during the incubation period. After this incubation the red cell suspension is decanted from each flask. The flasks are washed twice with 3.0 ml. of phosphate buffer sulution (pH 7.4) to remove unabsorbed red cells and 3.0 ml. of distilled water is then added to lyse the absorbed cells. The flasks are then further incubated at 37° C. for 30 minutes in a horizontal position and the flasks are rocked every 10 minutes. After this incubation the fluid contents of the pairs of flasks are combined to form an assay unit and are placed at room temperature for 15–20 minutes to allow settling of the cellular debris. A pair of control flasks identical with the above except for the absence of the test compound and virus inoculation are run concurrently. The resulting hemoglobin solutions from each assay unit are then read for optical density in a Beckman spectrophotometer at about 415 mμ. A test compound is considered active if any one of the tested levels it reduces the optical density reading by at least 50% relative to the virus control.

The hypolipidemic properties of the instant compounds is illustrated in the following assay:

Male Charles River rats (160–200 g.), having had free access to food and water, are administered a standard diet containing 2% DEAE — cellulose (Reeve Angel anion exchange resin) for 5 days. The rats then are sacrificed and their livers removed immediately. The livers are homogenized in a medium of 0.1 M potassium phosphate, pH 7.4, 0.004 m $MgCl_2$ and 0.03 M nicotinamide, and the microsomal-cytosol fraction obtained by centrifugation. 2.0 Ml. of the microsomal-cytosol fraction is incubated, at 37° C. for 90 minutes for measurement of cholesterol biosynthesis, in a standard assay mixture containing 10 micromoles of $C^{14}$- labeled mevalonic acid, 2 micromoles nicotinamide adenine dinucleotide 2 micromoles nicotinamide adenine dinucleotide phosphate, and 20 micromoles glucose-6-phosphate, and test compound, initially at 0.001 M, is added. All assays are run in duplicate with the assay to which no test compound is added serving as a control. Heat inactivated homogenate serves as blank for both control and test systems.

Reaction rate is determined per unit of time by the amount of $C^{14}$ label incorporated into the lipid fraction from the radioactive mevalonic acid. Results are reported as % inhibition (i.e. (Reaction Rate for Test Compound/Reaction Rate for Control) × 100).

The invention will appear more fully from the examples which follow. These examples are given by way of illustration only and are not to be construed as limiting the invention either in spirit or in scope as many modifications both in materials and methods will be apparent to those skilled in the art. In these examples temperatures are given in degrees Centigrade (°C.) and quantities of materials in parts by weight unless otherwise noted. Nuclear magnetic resonance data was obtained on a Varian A-60-A or Varian T60 instrument. Infrared spectra were recorded on a Beckman IR-12 grating spectrophotometer. Ultraviolet spectra were taken on a Beckman DK-2A.

EXAMPLE 1

To a solution of 400 parts of dihydroresorcinol in 2000 parts by volume of chloroform is added 161.2 parts of phosphorus trichloride and the resulting reaction mixture is stirred and heated at the reflux temperature in a nitrogen atmosphere for about 3½ hours. The mixture is then cooled and poured carefully into appromximately 1000 parts of a mixture of ice and water. The layers are separated and the aqueous phase is extracted with ether. The ether extracts are combined with the chloroform layer and the resulting organic solution is washed successively with 5% aqueous sodium hydroxide and water, then dried over anhydrous sodium sulfate. Removal of the solvent by distillation under reduced pressure affords the crude product, which is purified by distillation under reduced pressure, thus affording 3-chloro-2cyclohexen-1-one, boiling at about 65° under 3mm. pressure. Infrared absorption maxima in chloroform are observed at about 5.93 and 6.20 microns and a nuclear magnetic resonance peak in deuterochloroform at 6.23 parts per million.

EXAMPLE 2

To a mixture of 58 parts of sodium hydride and 1800 parts by volume of ethylene glycol dimethyl ether, under nitrogen, is added, at room temperature over a period of about 30 minutes, 198 parts of cyanoacetamide. That mixture is heated at the reflux temperature for about 30 minutes, then cooled to approximately room temperature and 145.2 parts of 3-chloro-2-cyclohexen1-one is added over a period of about 15 minutes. The mixture is stirred and heated at the reflux temperature for about 1 hour, then is cooled and a solution consisting of 20 parts by volume of methanol and 10 parts by volume of water is cautiously added dropwise. An additional 500 parts of water is then added and the organic solvents are removed by distillation under reduced pressure. Acidification of the residual aqueous solution to pH 1–2 results in precipitation of the product, which is isolated by filtration, then washed with cold water and dried. Purification of that crude product is effected by recrystallization from ethanol-water-ethyl acetate, thus affording α-cyano-3-oxo-1-cyclohexen-1-acetamide, melting at about 181°–183°. This compound exhibits an ultraviolet absorption maxima, in methanol, at about 370 mμ with a molecular extinction coefficient of about 21,900, infrared absorption peaks, in potassium bromide, at about 2.97, 4.55 and 6.02 microns and nuclear magnetic resonance maxima, in deuteropyridine, at about 1.73, 2.41 and 2.93 parts per million.

EXAMPLE 3

To a solution consisting of 40 parts of α-cyano-3-oxo-1-cyclohexen-1-acetamide in 125 parts by volume of dimethylformamide, in an atmosphere of nitrogen, is added dropwise, over a period of 10–15 minutes, 40 parts of dimethylformamide diethyl acetal. After the reaction mixture is stirred at room temperature for about 18 hours, 10 parts of water is added and the organic solvents are removed by distillation under reduced pressure. The residual oily product is extracted with dilute aqueous sodium hydroxide and the extract is washed several times with chloroform, then filtered to remove the small amount of insoluble material. Neutralization of the alkaline solution by the addition of dilute hydrochloric acid results in precipitation of the product, which is purified by recrystallization from aqueous acetone to afford 2,3,5,6,7,8-hexahydro-3,8-dioxo-4-isoquinolinecarbonitrile, melting above 290°. It is further characterized by ultraviolet absorption maxima at about 227, 232, 279 and 324 mμ with molecular extinction coefficients of 17,900, 16,000, 13,000 and 6,800, respectively, and by infrared absorption peaks, in potassium bromide, at about 2.87, 2.97, 4.48, 5.92, 6.03, 6.07, 6.23 and 6.45 μ and also by nuclear magnetic resonance peaks, in deuteropyridine, at approximately 1.92, 2.58, 2.97, and 8.72 parts per million.

EXAMPLE 4

A solution of 28.4 parts of 2,3,5,6,7,8hexahydro-3,8-dioxo-4-isoquinolinecarbonitrile in 500 parts by volume of 48% hydrobromic acid is heated at the reflux temperature in the absence of light for about 7 hours, following which time the solvent is removed by distillation under reduced pressure. The resulting residue is partitioned between chloroform and aqueous sodium chloride and the layers are separated. The aqueous phase is extracted several times with chloroform, then combined with the original chloroform layer. That organic solution is washed with aqueous sodium chloride, then dried over anhydrous sodium sulfate and stripped of solvent under reduced pressure to afford the crude product. The original aqueous layer is neutralized by the addition of sodium bicarbonate, then is extracted with chloroform. Evaporation of that chloroform extract to dryness affords additional product. The combined crude product is purified by recrystallization from aqueous acetone, thus affording pure 2,3,5,6,7,8-hexahydro-3,8isoquinolinedione, melting at about 246°–248° with decomposition. Ultraviolet absorption maxima are observed in methanol at 279 and 221 mμ with molecular extinction coefficients of about 16,700 and 13,500, respectively. In deuteropyridine, nuclear magnetic resonance peaks are displayed at about 1.96, 2.57, 2.92, 5.50 and 8.71 parts per million.

EXAMPLE 5

To a solution of 2.6 parts of 2,3,5,6,7,8hexahydro-3,8-isoquinolinedione in 375 parts by volume of dry benzene is added 2.3 parts of silver carbonate and 5 parts by volume of methyl iodide and the resulting mixture is heated at the reflux temperature in the absence of light under an atmosphere of nitrogen for about 4 hours. At the end of that time the mixture is cooled and filtered through diatomaceous earth to afford an organic solution, which is extracted several times with 6 N hydrochloric acid. Those acidic extracts are washed with chloroform, then made alkaline by the addition of aqueous sodium hydroxide and extracted with ether. The ether extracts are combined and washed with saturated aqueous sodium chloride, then dried over anhydrous sodium sulfate and stripped of solvent under reduced pressure. The resulting crude product is purified by recrystallization from water to yield 7 aza-6-methoxy-1tetralone, melting at about 55.5°–57°. This compound displays an ultraviolet absorption maximum at about 268 m$\mu$ with a molecular extinction coefficient of about 13,100, infrared absorption peaks, in chloroform, at about 5.92, 6.23, and 7.80 $\mu$ and nuclear magnetic resonance maxima, in deuterochloroform, at about 2.14, 2.64, 2.91, 3.97, 6.56 and 8.83 parts per million.

The aforementioned chloroform washings are evaporated to dryness under reduced pressure and the residual oil is extracted with benzene. The resulting organic solution is diluted with hexane to the point of incipient trubidity, then is decolorized with activated carbon. The decolorized solution is diluted with hexane, then cooled, thus affording crystalline 2-methyl-2,3,5,6,7,8hexahydro-3,8-isoquinolinedione, melting at about 94°–97°. It is characterized further by ultraviolet absorption maxima, in methanol, at about 224 and 281 m$\mu$ with molecular extinction coefficients of about 14,500 and 16,100, respectively, by infrared absorption maxima, in chloroform, at about 5.88 and 6.05 $\mu$ and by nuclear magnetic resonance peaks, in deuterochloroform, at about 2.10, 2.59, 2.84, 3.63, 6.35 and 8.28 parts per million.

EXAMPLE 6

To 43 parts of 2-bromo-3-dimethylaminopropene in 650 parts of toluene, cooled to about −10° under an atmosphere of nitrogen, is added 130 parts by volume of 2.04 N butyl lithium in hexane solution at a rate so as to maintain a temperature below −5° during the addition. After stirring for about 10 minutes, 9.8 parts of 7-aza6-methoxy-1-tetralone, dissolved in 22 parts of benzene, is added over a 10 minute period and the cooling bath is removed. After about 20 minutes when the temperature of the reaction mixture aas reached approximately 5°, the reaction mixture is quenched by the addition of 150 parts by volume of a saturated ammonium chloride solution. The two phases which form are separated and the aqueous solution is extracted with benzene. The combined extracts are subsequently extracted themselves with 5 portions of 5% aqueous formic acid solution. The acidic extracts are backwashed once with benzene before neutralization to pH 7 with aqueous ammonia and extraction with chloroform. Then the extracts are washed with a saturated sodium chloride solution and dried over anhydrous sodium sulfate. Upon solvent removal, crude product is obtained as an oil. The oil is dissolved into ether, and n-hexane is added until the solution become turbid. The solution then is filtered through diatomaceous earth and pure N,N-dimethylN-(2-[5,6,7,8-tetrahydro-8-hydroxy-3-methoxyisoquinol8-yl]prop-2-en-1-yl)amine is obtained upon reducing the volume of the solution and allowing the mixture to stand at room temperature. That material melts at about 66°–68° and is characterized by peaks in the nuclear magnetic resonance spectrum in deuteriochloroform at 119, 234, 261, 300, 383 and 493 Hertz and an ultraviolet absorption maximum in methanol at about 276 milimicrons with a molecular extinction coefficient of about 3,900.

EXAMPLE 7 A

To 7.1 parts of N,N-dimethyl-N-(2-[5,6,7,8tetrahydro-8-hydroxy-3-methoxyisoquinol-8-yl]prop-2-en1-yl)amine in 31 parts of benzene and 34.5 parts of pyridine is added 4.5 parts of phosphorous oxychloride, dropwise and at room temperature. That solution is stirred at room temperature for several hours, then cooled in an ice bath. 25 Parts of water slowly is added followed by enough 5% aqueous sodium hydroxide solution to bring the pH of the solution to about 10. Ether is added and the organic and aqueous layers separated. The aqueous layer is extracted with ether and the extracts washed with saturated sodium chloride and dried over anhydrous sodium sulfate. Approximately 200 parts of n-hexane is added to the solution, followed by a portion of charcoal. That mixture is filtered through diatomaceous earth to give a light yellow solution which, upon solvent removal, affords a yellow oil yielding upon crystallization N,N-dimethyl-N-(2-[5,6dihydro-3-methoxyisoquinol-8-yl]prop-2-en-1-yl)amine. A portion of that material is distilled and the distillate is taken up into methanol-water and upon standing yields crystals melting at about 42°–45°. That compound further exhibits an ultraviolet maximum in methanol at about 262 milimicrons with a molecular extinction coefficient of 12,900. It is further characterized by peaks in the nuclear magnetic resonance spectrum in deuteriochloroform at 134, 286, 336, 318, 357, 395 and 480 Hertz.

EXAMPLE 7 B

A solution of 0.04 part of N,N-dimethyl-N(2-[5,6,7,8-tetrahydro-8-hydroxy-3-methoxyisoquinol8-yl]prop-2-en-1-yl)amine and 0.5 part by volume of concentrated sulfuric acid is allowed to stand at room temperature for about 30 minutes. Then the reaction mixture is added to water and basified with aqueous ammonia. The solution is extracted with ether and the etheral extracts are washed with saturated sodium chloride solution, dried over anhydrous sodium sulfate and evaporated under reduced pressure to yield N,N-dimethyl-N-(2-[5,6dihydro-3-methoxyisoquinol-8-yl]prop-2-en-1-yl)amine, identical to the product of Example 7 A.

EXAMPLE 8

To a solution containing 4.3 parts of N,Ndimethyl-N-(2-[5,6-dihydro-3-methoxyisoquinol-8-yl]prop2-en-1-yl)amine in 88 parts of benzene is added 10 parts by volume of methyl iodide, and the mixture is allowed to stand at room temperature for 3½ hours. The precipitate which forms then is filtered, washed with additional benzene, and dried affording crude products which, upon recrystallization from acetone-ethylacetate, gives pure N,N,N-trimethyl-N-(2-[5,6-dihydro-3- methoxyisoquinol8-yl]prop-2-en-1-yl)ammonium iodide, melting at about 165°–169°. That material exhibits an ultraviolet maximum in methanol at about 263 milicrons with a molecular extinction coefficient of about 12,700 and maxima in the nuclear magnetic resonance spectrum in deuteriochloroform at about 208, 236, 280, 353, 373, 381, 397 and 472 Hertz.

EXAMPLE 9 A 5.8 Parts of N,N,N-trimethyl-N-(2-[5,6-dihydro3-methoxyisoquinol-8-yl]prop-2-en-1-yl)ammonium iodide is dissolved in a mixture of 64 parts of methanol and 20 parts of water, then treated with 1.9 parts of silver oxide. The solution is stirred in the absence of light for 1 hour, then filtered through diatomaceous earth. The filtrate is treated with 2.0 parts of 2-methylcyclopentane-1,3dione, and the solvent is removed under reduced pressure at about 50°.

The oily residue which remains is taken up into 26 parts of dioxane, and 132 parts of xylene is added, followed by 4 parts by volume of triethylamine. The solution is heated to reflux temperature and refluxed overnight under a nitrogen atmosphere, then 5% aqueous sodium hydroxide solution is added. The layers are separated and the organic phase is washed with saturated sodium chloride and extracted with 2.5% aqueous formic acid. The acidic extracts are backwashed with benzene and combined. After washing with saturated sodium chlorine solution, drying over anhydrous sodium sulfate and removing solvent, an oil remains which crystallizes upon scratching to afford crude product. Pure 5,6-dihydro-3-methoxy-8-[3-(2methyl-1,3-dioxocyclopent-2-yl)prop-1-en-2-yl]isoquinoline is obtained upon recrystallization from acetone. That material is characterized by maxima in the ultraviolet spectrum in methanol at 261 milimicrons with a molecular extinction coefficient at about 12,200, and maximum in the nuclear magnetic resonance spectrum in deuteriochloroform at 64, 156, 265, 237, 306, 345, 395 and 470.

EXAMPLE 9 B

A solution containing 0.75 parts of 2-methylcyclopentane-1,3-dione in 19 parts of dimethylformamide is treated sequentially with 1.0 part by volume of triethylamine and 1.9 parts of N,N,N-trimethyl-N-(2-[5,6-dihydro-3-methoxyisoquinol-8-yl]prop-2-en-1-yl)ammonium iodide. The resulting homogeneous solution is heated at about 135° for 4 ¾ hours. It is allowed to cool to room temperature and solvent is removed under reduced pressure. The remaining material is diluted with water-ether and enough 5% sodium hydroxide solution is added to bring the pH to 10. The aqueous and organic layers are separated and the aqueous layer is extracted with ether. The extracts are washed sequentially with 5% sodium hydroxide solution, 2.5% aqueous formic acid and saturated sodium chloride solution, then dried over anhydrous sodium sulfate. Upon solvent removal, an oil remains which is taken into ether. Then n-hexane is added until the solution becomes turbid. Charcoal is added and the mixture is filtered. Solvent is removed under reduced pressure to yield an oil which crystallizes upon standing. Recrystallization from acetone-water gives pure 5,6-dihydro-3-methoxy-8-[3-(2-methyl-1,3-dioxocyclopent-2-yl)prop-1-en-2-yl]isoquinoline, which is identical to the product obtained in Example 9 A.

EXAMPLE 10

To 40 parts by volume of concentrated sulfuric acid, cooled to about −5° with a cooling bath, is added 2.4 parts of 5,6-dihydro-3-methoxy-8-[3-(2-methyl-1,3dioxocyclopent-2-yl)prop-1-en-2-yl]isoquinoline, portionwise at a rate such that the temperature does not exceed 10°. After the additions are completed, the cooling bath is removed and the solution allowed to warm to room temperature over approximately a 20 minute period. The solution then is added to 100 parts of water, cooled in an ice bath, and basified with ammonium hydroxide to afford a precipitate, which is recovered by filtration. That material is recrystallized from acetone to give pure compound, dl-2-aza-3-methoxy-11β-methylestra-1,3,5(10),8(14),9(11),15-hexaen-17-one, melting at about 197°–198.5°. That material is characterized by maxima in the ultraviolet spectrum in methanol at about 244 milimicrons with a molecular extinction coefficient of 19,000, 280 milimicrons with a molecular extinction coefficient of 15,500, and 372 milimicrons with a molecular extinction coefficient of 8200. It is further characterized by maxima in the nuclear magnetic resonance spectrum in deuteriochloroform at 67, 130, 238, 372, 397, 478 and 491 Hertz, and is represented structurally by the following formula

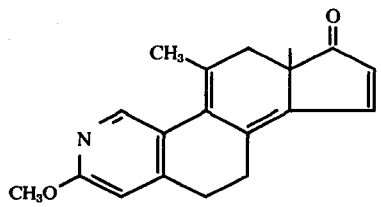

EXAMPLE 11

A solution of 2.1 parts of dl-2-aza-3-methoxy-11β-methylestra-1,3,5(10),8(14),9(11),15-hexaen-17-one in 66 parts of benzene and 36 parts of ethyl ether, cooled to 0°, is treated with 12 parts of a 20% diisobutyl aluminum hydride in toluene solution. The reducing agent is added dropwise over a 10 minute period. The initially heterogeneous solution becomes homogeneous and is stirred for about 15 minutes before destroying reducing agent with isopropyl alcohol. Water, acidified with a small quantity of hydrochloric acid, is added to form 2 layers. The slightly acidic aqueous layer is extracted with benzene and the pH of the aqueous solution then is adjusted to approximately 6.5 to 7 with ammonium hydroxide. The aqueous layer then is extracted with chloroform. The extracts are combined and upon solvent removal an oil remains which is triturated with methanol to give crude crystalline product. Pure dl-2-aza-3-methoxy-11β-methylestra-1,3,5(10),8(14),9(11),15-hexaen-17β-ol, melting at about 95°–100°, is obtained upon recrystallization from methanol. That material is characterized by maxima in the ultraviolet spectrum in methanol at about 257 milimicrons with a molecular extinction coefficient of about 30,700 and 263 milimicrons with a molecular extinction coefficient of about 29,700. It further is characterized by maxima in the nuclear magnetic resonance spectrum in deuteriochloroform at about 48, 129, 238, 264, 364, 389, 396 and 491 Hertz and is represented structurally by the following formula

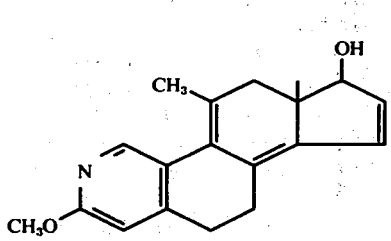

EXAMPLE 12

A mixture consisting of 1.0 part of dl-2-aza-3-methoxy-11β-methylestra-1,3,5(10),8(14),9(11),15-hexaen-17β-ol, 200 parts by volume of benzene, and 0.5 part of 5% palladium-on-calcium carbonate catalyst is stirred in a hydrogen atmosphere at room temperature and atmospheric pressure until approximately a molecular equivalent of hydrogen has been absorbed. The solvent is removed under reduced pressure to yield an oil which is taken up into denatured ethanol. Upon cooling, dl-2-aza-3-methoxy-11β-methylestra-1,3,5(10),8(14),9(11)-pentaen-17β-ol forms as yellow crystals. That material exhibits maxima in the ultraviolet spectrum in methanol at about 291 milimicrons with a molecular extinction coefficient of about 6860, 242 milimicrons with a molecular extinction coefficient of about 21,900 and 247 milimicrons with a molecular extinction coefficient of about 20,900. It further is characterized by maxima in the nuclear magnetic resonance spectrum in deuterio chloroform at about 55, 122, 135, 237, 243 and 488 Hertz. It is structurally represented by the following formula.

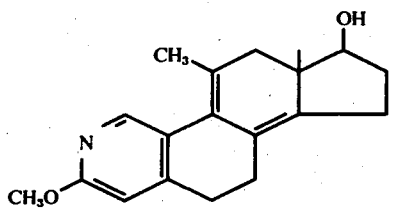

EXAMPLE 13

To a solution of 3.7 parts of dl-2-aza-3-methoxy-11β-methylestra-1,3,5(10),8(14),9(11)-pentaen-17β-ol in 79 parts of ethanol is added 1.8 parts of 5% palladium-on-alumina catalyst and that mixture is shaken with hydrogen until a molecular equivalent of hydrogen has been absorbed. The catalyst is removed by filtration and the solvent removed under reduced pressure to give an oil, which when taken up in methanol and cooled yields crystalline dl-2-aza-3-methoxy-11β-methylestra-1,3,5(10),8-tetraen-17β-ol, melting at about 164°-167.5°. That material exhibits a maxima in the ultraviolet spectrum in methanol at about 267 milimicrons with a molecular extinction coefficient of about 16,400. It further is characterized by maxima in the nuclear magnetic resonance spectrum in deuteriochloroform at about 56, 75, 236, 393, and 477 Hertz.

EXAMPLE 14

To 50 parts by volume of freshly distilled ammonia, cooled to −78° under a nitrogen atmosphere, is added 0.55 part of sodium metal in small pieces. The mixture is stirred for approximately 15–30 minutes, then 0.30 parts of dl-2-aza-3-methoxy-11β-methylestra-1,3,5(10), 8-tetraen-17β-ol in 18 parts of tetrahydrofuran is added to the deep blue solution over a 5 minute period. The reaction mixture is stirred at −78° for about 30 minutes, then 2.0 parts of ammonium chloride is added. The cooling bath is removed and the reaction mixture is allowed to warm to about −33° at which point the ammonia is distilled off. A portion of ether is added as the ammonia evaporates and after evaporation, saturated sodium chloride solution is added, and the other layer is separated from the aqueous phase. The organic phase is washed with additional sodium chloride solution and dried over anhydrous sodium sulfate. Upon solvent removal, desired product and crude dl-2-aza-3-methoxy-11β-methylestra-2,4(10)-dien-17β-ol remains as an oil. The crude oil is taken up in a mixture of 5 parts by volume of acetone and 5 parts by volume of benzene, and to this solution is added 0.250 part of dichlorodicyanobenzoquinone. The reaction mixture is stirred at room temperature for about 15 minutes, after which time 25 parts by volume of a 10% sodium bisulfite solution and a portion of ether is added. The two layers are separated and the organic phase is washed with 5% sodium hydroxide solution and saturated sodium chloride solution and dried over anhydrous sodium sulfate. The dried solution is treated with activated charcoal and filtered through diatomaceous earth. Solvent removal gives an oil which, upon crystallization from methanol and recrystallization from ether-methanol, gives pure dl-2-aza-3-methoxy-11β-methylestra-1,3,5(10)-trien-17β-ol, melting at about 168°-169°. That material is characterized by a maximum in the ultraviolet spectrum in methanol at about 278 milimicrons with a molecular extinction coefficient of about 3,760 and maxima in the nuclear magnetic resonance spectrum in deuteriochloroform at about 55, 56, 234, 385, and 477 Hertz. That compound is represented structurally by the following formula.

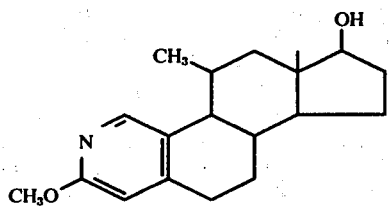

EXAMPLE 15

0.100 Part of dl-2-aza-3-methoxy-11β-methylestra-1,3,5(10)-trien-17β-ol in 1 part by volume of dimethyl sulfoxide containing 0.25 part by volume of triethylamine is vigorously stirred, then treated with 0.15 part of sulfur trioxide-pyridine salt. The reaction mixture is stirred for 20 minutes to afford an oil, which upon continued stirring becomes a red solid. The solid is recovered and recrystallized from methanol to give dl-2-aza-3-methoxy-11β-methylestra-1,3,5(10)-trien-17-one, melting at about 155°-160°, and characterized by a maximum in the ultraviolet spectrum at about 276 milimicrons with a molecular extinction coefficient of about 3700 and peaks in the nuclear magnetic resonance spectrum at about 54, 62, 65, 236, 391 and 478 Hertz. That compound is represented structurally by the following formula.

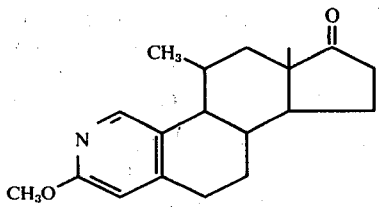

EXAMPLE 16

To 4 parts of powdered potassium hydroxide in 8.9 parts of tetrahydrofuran, at about 0°, is added 0.73 part of ethanol, and the solution is stirred for about ½ hour while maintaining the temperature at about 0°. Acetylene gas, scrubbed with water and concentrated sulfuric acid, is passed through the solution at this temperature for 20–25 minutes. To this is added dropwise a solution of 0.90 part of 2-aza-3-methoxy-11β-methylestra-1,3,5(10)-trien-17-one in about 3 parts of tetrahydrofuran, and the resulting reaction mixture is stirred for 1½ hours at the temperature of 0°–5° while continually bubbling acetylene through the solution. Then water is added, and the aqueous phase extracted with ether. The extracts are washed with saturated salt solution and dried. Charcoal is added and, after filtering and solvent removal, the oily residue which remains is chromatographed over aluminum oxide to yield the crude product. 2-Aza-17α-ethynyl-3-methoxy-11β-methylestra-1,3,5(10)-trien-17β-ol is obtained upon recrystallized from a hexane-acetone mixture. This compound is represented by the following structural formula.

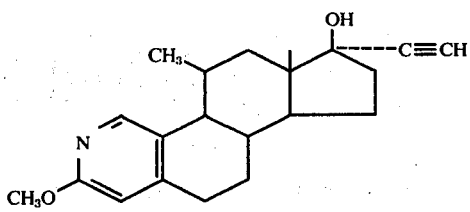

EXAMPLE 17

To 1.0 part of 2-aza-3-methoxy-11β-methylestra-1,3,5(10)-trien-17-one in about 30 parts of tetrahydrofuran, cooled to about 0° and under a nitrogen atmosphere, is added, dropwise over a period of about 10 minutes, 0.84 part of methyl magnesium bromide. The mixture is allowed to come to room temperature and is stirred for about 3–5 hours. Water is added, followed by enough ether and sodium hydroxide to form two layers, and the two phases are separated. The ethereal extracts are washed with saturated salt solution, dried, and upon solvent removal, an oil remains. 2-Aza-3-methoxy-11β,17α-dimethylestra-1,3,5(10)-trien-17β-ol is obtained after oil is chromatographed over aluminum oxide. That compound is represented by the following structural formula

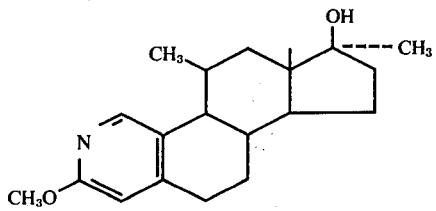

EXAMPLE 18

An equivalent quantity of 1-propynyl magnesium bromide is substituted in the procedure of Example 16, and 2-aza-3-methoxy-11β-methyl-17α-(1-propynyl)estra-1,3,5(10)-trien-17β-ol is produced.

EXAMPLE 19

Substitution of an equivalent quantity of ethyl magnesium bromide in the procedure of Example 17 yields 2-aza-17α-ethyl-3-methoxy-11β-methylestra-1,3,5(10)-trien-17β-ol.

EXAMPLE 20

To a solution of ethyl magnesium bromide, prepared from 8.2 parts of ethyl bromide and 1.8 parts of magnesium turnings in 150 parts of volume of tetrahydrofuran, is added a solution containing 12 parts of 3-tetrahydropyran-2'-yloxyprop-1-yne in 100 parts by volume of tetrahydrofuran. That reaction mixture is heated at the reflux temperature for about 5 minutes, then is allowed to stand at room temperature for about 2 hours. At the end of that time a solution containing 10 parts of 2-aza-3-methoxy-11β-methylestra-1,3,5(10)-trien-17-one in 150 parts of volume of tetrahydrofuran is added. The resulting reaction mixture is stirred at room temperature for about 2 hours, then is poured carefully into saturated aqueous ammonium chloride. The resulting product is isolated by extraction of that aqueous mixture with methylene chloride.

To a suspension consisting of 10 parts of lithium aluminum hydride and 200 parts by volume of ether is added, dropwise with stirring, 10 parts of the latter product, i.e. 2-aza-3-methoxy-11β-methyl-17α-(3-tetrahydropyran-2'-yloxypropynyl)estra-1,3,5(10)-trien-17β-ol, dissolved in 200 parts by volume of ether. The resulting suspension is heated at the reflux temperature with stirring for about 2½ hours, at the end of which time the excess reducing agent is decomposed by the addition of acetone. The metal salts are precicptated by the addition of saturated aqueous sodium sulfate and solid sodium sulfate and the resulting mixture is filtered. The filter cake is washed with methylene chloride and the filtrate is dried over anhydrous sodium sulfate and evaporated to dryness under reduced pressure. The resulting residue is mixed with 200 parts by volume of 1% methanolic hydrogen chloride solution and that mixture is allowed to stand at room temperature for about 15 minutes. At the end of that time approximately 2,000 parts of water is added and the aqueous mixture is extracted with methylene chloride. The organic extracts are washed with water, dried over anhydrous sodium sulfate and evaporated to dryness under reduced pressure, thus affording 2-aza-3-methoxy-11β-methyl-17α-propadienylestra-1,3,5(10)-trien-17β-ol, represented by the following structural formula

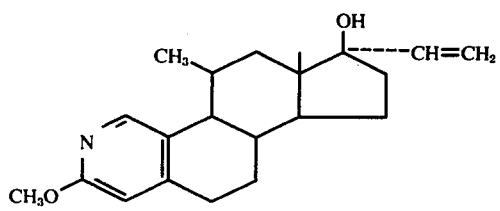

EXAMPLE 21

Substitution of an equivalent quantity of ethyl iodide, cyclopentyl iodide or cyclohexyl iodide for the methyl iodide utilized in the procedure of Example 5 affords, respectively, 7-aza-6-ethoxy-1-tetralone, 7-aza-6-cyclopentyloxy-1-tetralone and 7-aza-6-cyclohexyloxy-1-tetralone.

EXAMPLE 22

The products described in Example 21 are treated according to the procedures outlined in Examples 6–10 to yield, respectively, dl-2-aza-3-ethoxy-11β-methylestra-1,3,5(10),8(14),9(11),15-hexaen-17-one; dl-2-aza-3-cyclopentyloxy-11-methylestra-1,3,5(10),8(14),9(11),15-hexaen-17-one; and dl-2-aza-3-cyclohexyloxy-11β-methylestra-1,3,5(10),8(14),9(11),15-hexaen-17-one.

EXAMPLE 23

The compounds of Example 22 are treated according to the procedure described in Example 11 to afford, respectively, dl-2-aza-3-ethoxy-11β-methylestra-1,3,5(10),8(14), 9(11),15-hexaen-17β-ol; dl-2-aza-3-cyclopentyloxy-11β-methylestra-1,3,5(10),8(14),9(11),15-hexaen-17β-ol; and dl-2-aza-3-cyclohexyloxy-11β-methylestra-1,3,5(10),8(14),9(11),15-hexaen-17β-ol.

EXAMPLE 24

The compounds of Example 23 are treated according to the procedure described in Example 12 to afford, respectively, dl-2-aza-3-ethoxy-11β-methylestra-1,3,5(10),8(14), 9(11)-pentaen-17β-ol; dl-2-aza-3-cyclopentyloxy-11β-methylestra-1,3,5(10),8(14),9(11)-pentaen-17β-ol; and dl-2-aza-3-cyclohexyloxy-11β-methylestra-1,3,5(10),8(14),9(11)-pentaen-17β-ol.

EXAMPLE 25

The compounds of Example 24 are treated according to the procedures described in Examples 13 and 14 to afford, respectively, initially the intermediates dl-2-aza-3-ethoxy-11β-methylestra-2,5(10)-dien-17β-ol; dl-2-aza-3-cyclopentyloxy-11β-methylestra-2,5(10)-dien-17β-ol; and dl-2-aza-3-cyclohexyloxy-11β-methylestra-2,5(10)-dien-17β-ol, and then the instant dl-2-aza-3-ethoxy-11β-methylestra-1,3,5(10)-trien-17β-ol; dl-2-aza-3-cyclopentyloxy-11β-methylestra-1,3,5(10)-trien-17β-ol; and dl-2aza-3-cyclohexyloxy-11β-methylestra-1,3,5(10)-trien-17β-ol.

EXAMPLE 26

The products of Example 25 are treated according to the procedure of Example 15 to afford, respectively, dl-2-aza-3-ethoxy-11β-methylestra-1,3,5(10)-trien-17-one, dl-2-aza-3-cyclopentyloxy-11β-methylestra-1,3,5(10)-trien
17-one, dl-2-aza-3-cyclohexyloxy-11β-methylestra-1,3,5(10)-trien-17-one.

EXAMPLE 27

When an equivalent quantity of 2-aza-3-cyclopentyloxy-11β-methylestra-1,3,5(10)-trien-17-one is substituted in the procedure of Example 16, there is obtained 2-aza-3-cyclopentyloxy-17α-ethynyl-11β-methylestra-1,3,5(10)-trien-17β-ol.

EXAMPLE 28

To 1 part of dl-2-aza-3-methoxy-11β-methylestra-1,3,5(10)-trien-17β-ol in 10 parts of pyridine is added an excess of acetic anhydride. The mixture is stirred for approximately 3 to 4 hours whereupon 100 parts of water is added with cooling to yield, upon filtering, dl-2-aza-3-methoxy-11β-methylestra-1,3,5(10)-trien-17β-ol 17 -acetate.

EXAMPLE 29

Substitution of an equivalent quantity of 2-bromo-1-dimethylamino-2-butene in the procedure of Example 6 affords N,N-dimethyl-N-(2-[5,6,7,8-tetrahydro-8-hydroxy-3-methoxyisoquinol-8-yl]but-2-en-1-yl)amine.

EXAMPLE 30

Treating the product of Example 29 according to the procedures outlined in Examples 7–10 affords dl-2-aza-11β-ethyl-3-methoxyestra-1,3,5(10),8(14),9(11),15-hexaen-17-one.

EXAMPLE 31

The product of Example 30 is treated according to the procedure of Example 11 to yield dl-2-aza-11β-ethyl-3-methoxyestra-1,3,5(10),8(14),9(11),15-hexaen-17β-ol.

EXAMPLE 32

The product of Example 31 is treated according to the procedure of Example 12 to afford dl-2-aza-11β-ethyl-3-methoxyestra-1,3,5(10),8(14),9(11)-pentaen-17β-ol.

EXAMPLE 33

The product of Example 32 is treated sequentially according to the procedures of Examples 13 and 14 to yield dl-2-aza-11β-ethyl-3-methoxyestra-1,3,5-(10)-trien-17β-ol.

EXAMPLE 34

1 Part of dl-2-aza-3-methoxy-11β-methylestra-1,3,5(10)-trien-17-one is refluxed in 16% hydrobromic acid solution for about 3–24 hours to afford dl-2-aza-11β-methylestra-1(10),4-diene-3,17-dione, which is recovered by filtration after neutralization of the acidic medium.

EXAMPLE 35

To a suspension containing 1 part of 2-aza-11β-methylestra-1(10),4-diene-3,17-dione and 0.7 part of t-butyl-dimethylchlorosilane in 10 parts by volume of dioxane is added dropwise 0.7 part of triethylamine dissolved in 5 parts by volume of dioxane. The resulting reaction mixture is stirred at room temperature for about 16 hours and the suspension is filtered to remove triethylamine hydrochloride. The filter cake is washed with dioxane and the filtrate is concentrated to dryness under reduced pressure. The resulting residue is purified by recrystallization from ethyl acetate-hexane, thus affording 2-aza-11β-methyl-3-(t-butyl-dimethyl-silyloxy)estra-1,3,5(10)-trien-17-one.

What is claimed is:

1. A compound of the formula

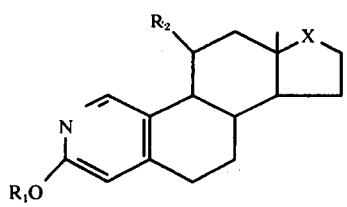

wherein $R_1$ is a lower alkyl group having 1 to 7 carbon atoms inclusive or a cycloalkyl group having 4–8 carbon atoms inclusive, $R_2$ is a lower alkyl group having 1 to 4 carbon atoms inclusive, and X is a carbonyl group or a group of the formula

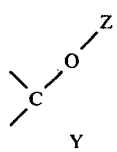

wherein Y is hydrogen, a lower alkyl group having 1 to 7 carbon atoms inclusive, a lower 1-alkynyl group having 2 to 7 carbon atoms inclusive or a propadienyl group and Z is hydrogen.

2. As in claim 1, a compound of the formula

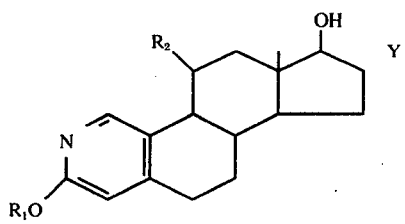

wherein $R_1$ is a lower alkyl group having 1 to 7 carbon atoms inclusive or a cycloalkyl group having 4–8 carbon atoms inclusive and Y is a lower alkyl group having 1 to 7 carbon atoms inclusive.

3. As in claim 1, a compound of the formula

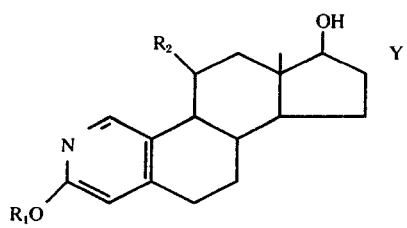

wherein $R_1$ is a lower alkyl group having 1 to 7 carbon atoms or a cycloalkyl group having 4–8 carbon atoms inclusive and Y is a lower 1-alkynyl group having 2 to 7 carbon atoms inclusive.

4. As in claim 1, the compound which is 2-aza-3-methoxy-11β-methylestra-1,3,5(10)-trien-17-one.

5. As in claim 1, the compound which is 2-aza-3-methoxy-11β-methylestra-1,3,5(10)-trien-17β-ol.

6. As in claim 1, the compound which is 2-aza-17α-ethynyl-3-methoxy-11β-methylestra-1,3,5(10)-trien-17β-ol.

7. As in claim 1, the compound which is 2-aza-3-methoxy-11β-methyl-17α-methylestra-1,3,5(10)-trien-17β-ol.

8. As in claim 1, the compound which is 2-aza-3-cyclopentyloxy-11β-methylestra-1,3,5(10)-trien-17-one.

9. As in claim 1, the compound which is 2-aza-3-cyclopentyloxy-17α-ethynyl-11β-methylestra-1,3,5(10)-trien-17β-ol.

10. A compound of the formula

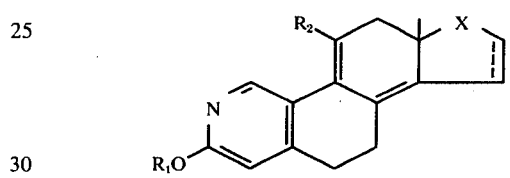

wherein $R_1$ is a lower alkyl group having 1–7 carbon atoms inclusive or a cycloalkyl group having 4–8 carbon atoms inclusive, $R_2$ is a lower alkyl group having 1–4 carbon atoms inclusive, X is a carbonyl or β-hydroxymethylene group and the dotted line represents an optionally doubly-bonded linkage.

11. A compound as in claim 10 of the formula

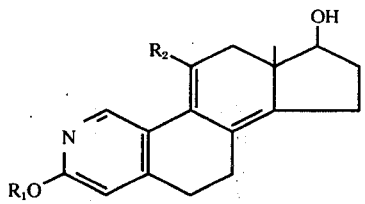

wherein $R_1$ and $R_2$ are defined as in claim 10.

12. A compound of the formula

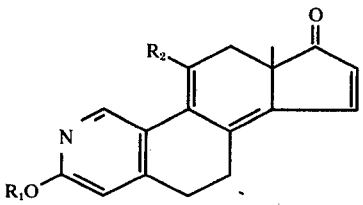

wherein $R_1$ and $R_2$ are defined as in claim 10.

13. A compound as in claim 10 of the formula

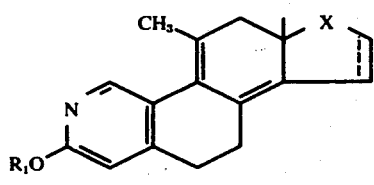
wherein $R_1$ and X are as defined in claim 10 and the dotted line represents an optionally doubly bonded linkage.
14. A compound as in claim 10 of the formula
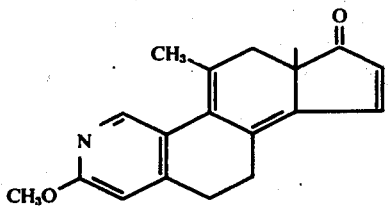
* * * * *